(12) United States Patent
Morris

(10) Patent No.: US 6,681,134 B2
(45) Date of Patent: *Jan. 20, 2004

(54) THERAPY-SELECTION METHODS FOR IMPLANTABLE HEART MONITORS

(75) Inventor: Milton M. Morris, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 114 days.

This patent is subject to a terminal disclaimer.

(21) Appl. No.: 09/955,491

(22) Filed: Sep. 18, 2001

(65) Prior Publication Data

US 2002/0111654 A1 Aug. 15, 2002

Related U.S. Application Data

(63) Continuation of application No. 09/343,924, filed on Jun. 30, 1999, now Pat. No. 6,314,321.

(51) Int. Cl.⁷ .............................................. A61N 1/365
(52) U.S. Cl. .............................. 607/9; 607/14; 600/518
(58) Field of Search ........................... 607/4, 9, 14, 17, 607/25; 600/516, 518

(56) References Cited

U.S. PATENT DOCUMENTS

| | | | |
|---|---|---|---|
| 4,940,054 A | 7/1990 | Grevis et al. | ......... 128/419 PG |
| 5,012,814 A | 5/1991 | Mills et al. | ................. 128/691 |
| 5,107,850 A | 4/1992 | Olive | ......................... 128/705 |
| 5,184,614 A | 2/1993 | Collins et al. | ......... 128/419 PG |
| 5,193,535 A | 3/1993 | Bardy et al. | ............. 128/419 D |
| 5,193,550 A | 3/1993 | Duffin | ........................ 129/697 |

(List continued on next page.)

FOREIGN PATENT DOCUMENTS

| WO | 95/09029 | 4/1995 | |
|---|---|---|---|
| WO | 98/48891 | 11/1998 | .......... A61N/1/362 |

OTHER PUBLICATIONS

Jenkins, et al., "Diagnosis of Atrial Fibrillation Using Electrogram from Chronic Leads: Evaluation of Computer Algorithm", *PACE*, 11, pp. 622–631, (1988).

Jung, et al., "Discrimination of Sinus Rhythm, Atrial Flutter, and Atrial Fibrillation Using Bipolar Endocardial Signals", *Journal of Cardiovascular Electrophysiology*, 9 (7), pp. 685–695, (Jul. 1998).

(List continued on next page.)

Primary Examiner—Jeffrey R. Jastrzab
(74) Attorney, Agent, or Firm—Schwegman, Lundberg, Woessner & Kluth, P.A.

(57) ABSTRACT

Thousands of patients prone to irregular and sometimes life threatening heart rhythms have miniature heart-monitoring devices, such as defibrillators and cardioverters, implanted in their chests. These devices detect onset of abnormal heart rhythms and automatically apply one or more shocks to their hearts. When properly sized and timed, the shocks restore normal heart function without human intervention. A critical part of these devices is the monitoring circuitry, which includes a microprocessor and stored instructions, or algorithms, that govern how the devices interpret and react to electrical signals indicative of abnormal heart rhythms. Often, the algorithms are too simple or too complex. Algorithms that are too simple lead to unnecessary shocking of the heart, while those that are too complex consume considerable battery power. Accordingly, the inventor devised a relatively simple and accurate algorithm for determining appropriate therapy options. One version of the algorithm computes three statistics—a range statistic, a minimum interval statistic, and a dispersion index—from a set of depolarization intervals. This algorithm defines the range statistic as the difference between largest and smallest depolarization intervals, the minimum interval as the smallest of the intervals, and the dispersion index as the standard deviation of the intervals. A scalar interval dispersion assessment, based on the three statistics, is then compared to a threshold to identify a rhythm as a flutter or fibrillation. The three statistics can also define a point in a three-dimensional space, with rhythm identification based on relative position of the point and a surface in the space.

19 Claims, 4 Drawing Sheets

U.S. PATENT DOCUMENTS

| | | |
|---|---|---|
| 5,311,874 A | 5/1994 | Baumann et al. ............ 128/705 |
| 5,437,285 A | 8/1995 | Verrier et al. ................ 128/702 |
| 5,474,574 A | 12/1995 | Payne et al. ..................... 607/7 |
| 5,522,850 A | 6/1996 | Yomtov et al. ................. 607/5 |
| 5,560,370 A | 10/1996 | Verrier et al. ............... 128/705 |
| 5,605,159 A | 2/1997 | Smith et al. ................. 128/702 |
| 5,613,495 A | 3/1997 | Mills et al. .................. 128/696 |
| 5,674,251 A | 10/1997 | Combs et al. ................... 607/4 |
| 5,676,153 A | 10/1997 | Smith et al. ................. 128/702 |
| 5,683,429 A | 11/1997 | Mehra .......................... 602/14 |
| 5,718,235 A | 2/1998 | Golosarsky et al. ......... 128/708 |
| 5,741,304 A | 4/1998 | Patwardhan et al. ........... 607/5 |
| 5,749,901 A | 5/1998 | Bush et al. ..................... 607/5 |
| 5,755,739 A | 5/1998 | Sun et al. ..................... 607/14 |
| 5,759,196 A | 6/1998 | Hess et al. .................... 607/14 |
| 5,842,997 A | 12/1998 | Verrier et al. ............... 600/518 |
| 5,991,657 A | 11/1999 | Kim .............................. 607/5 |
| 5,991,662 A | 11/1999 | Kim et al. ..................... 607/27 |
| 5,999,850 A | 12/1999 | Dawson et al. ................. 607/4 |
| 6,041,251 A | 3/2000 | Kim et al. ................... 600/518 |
| 6,047,210 A | 4/2000 | Kim et al. ..................... 607/4 |
| 6,052,617 A | 4/2000 | Kim ........................... 600/518 |
| 6,058,328 A | 5/2000 | Levine et al. ................. 607/14 |

OTHER PUBLICATIONS

Morris, et al., "Intracardiac Electrogram Transformation: Morphometric Implications for Implantable Devices", *Journal of Electrocardiology, 29 Supplement*, pp. 124–129, (1996).

Schuller, et al., "Far Field R–Wave Sensing—An Old Problem Repeating", *PACE, 19, Part II*, NASPE Abstract No. 264, p. 631, (1996).

Seim, G., et al., "Classification of Atrial Flutter and Atrial Fibrillation Using an Atrial Dispersion Index (ADI)", *Guidant CRM Therapy Research Peer Review Report Revision 2.0*, 27 p., (Jan. 6, 1999).

Stephany, et al., "Real–Time Estimation of Magnitude–Square Coherence for Use in Implantable Devices", *IEEE Computers in Cardiology*, pp. 375–378, (1992).

Swiryn, S., et al., "Detection of Atrial Fibrillation by Pacemakers and Antiarrhythmic Devices", *Nonpharmacological Management of Atrial Fibrillation, Chapter 21*, Futura Publishing Co, Inc. Armonk, NY, pp. 309–318, (1997).

THERAPY-SELECTION METHODS FOR IMPLANTABLE HEART MONITORS

CROSS REFERENCE TO RELATED APPLICATION(S)

This application is a continuation of U.S. patent application Ser. No. 09/343,924, filed on Jun. 30, 1999, now U.S. Pat. No. 6,314,321 the specification of which is incorporated herein by reference.

TECHNICAL FIELD

The present invention concerns heart-monitoring devices and methods, particularly implantable defibrillators, pacemakers, and cardioverters, and methods for processing heart-signal data.

BACKGROUND OF THE INVENTION

Since the early 1980s, thousands of patients prone to irregular and sometimes life threatening heart rhythms have had miniature heart-monitoring devices, such as defibrillators, pacemakers, and cardioverters, implanted in their bodies. These devices detect onset of abnormal heart rhythms and automatically apply corrective electrical therapy, specifically one or more bursts of electric current, to their hearts. When the bursts of electric current are properly sized and timed, they restore normal heart function without human intervention, sparing patients considerable discomfort and often saving their lives.

The typical implantable heart-monitoring device includes a set of electrical leads, which extend from a sealed housing through the veinous system into the inner walls of a heart after implantation. Within the housing are a battery for supplying power, a capacitor for delivering bursts of electric current through the leads to the heart, and heart-monitoring circuitry for monitoring the heart and determining not only when and where to apply the current bursts but also their number and magnitude.

The monitoring circuitry generally includes a microprocessor and a memory that stores a computer program. The computer program, or more generally the signal-processing algorithm, instructs the microprocessor how to interpret electrical signals that naturally occur during expansion and contraction of a heart muscle. The algorithm also instructs the processor what, if any, electrical therapy should be given to correct abnormal heart rhythms.

In general, these algorithms are either too complex or too simple. Complex algorithms require considerable processing time and power to implement. Greater processing time generally lengthens device response time, and greater power requirements generally shorten the lifespan of the batteries in these devices. Simple algorithms, though faster and less-power-hungry, are often less accurate in interpreting heart electrical signals, leading devices to overlook some heart conditions, to apply unnecessary electrical therapy, or to apply the wrong type of therapy.

Accordingly, there is a continuing need for algorithms that are not only energy-efficient, but also highly accurate in diagnosing and treating abnormal heart rhythms.

SUMMARY OF THE INVENTION

To address this and other needs, the inventor has devised new methods for processing heart electrical signals and selecting appropriate therapy options. An exemplary embodiment of the method computes three statistics—a range statistic, a minimum interval statistic, and a dispersion index—from a set of atrial depolarization intervals, which indicate the time between successive depolarizations in the atria of a heart. More particularly, after rejecting the two shortest and two longest intervals, the exemplary embodiment defines the range statistic as the difference between a first and last one of the remaining intervals, the minimum interval as the smallest of the remaining intervals, and the dispersion index as the standard deviation of the remaining intervals.

The exemplary embodiment then uses the three statistics to compute a number, which the inventor calls an interval dispersion assessment (IDA), to quantify the current rhythmic state of a heart. If this number is greater than a threshold value, typically experimentally determined, the exemplary embodiment interprets the current rhythmic state of the heart as, for example, an atrial or ventricular fibrillation. On the other hand, if the number is less than the threshold value, the exemplary embodiment interprets the rhythmic state as an atrial flutter or ventricular tachycardia.

Other exemplary methods use the three statistics to define a point in a three-dimensional space. The space is defined by three axes which correspond to the three statistics, making it possible to plot the "position" of the point in the space. These methods also define a surface, for example, a plane in the space, based on a set of values for the three statistics. The set of values are determined using a threshold value as a constraint. Position of the point above or below the surface can then be used to identify a rhythmic state corresponding to the point as, for example, an atrial flutter or atrial fibrillation or as a ventricular tachycardia or ventricular fibrillation.

Ultimately, the exemplary method and other methods embodying teachings of the present invention can be incorporated into medical devices, for example, pacemakers, defibrillators, or cardioverter defibrillators, to identify and treat abnormal rhythmic conditions both efficiently and accurately.

DESCRIPTION OF THE PREFERRED EMBODIMENTS

The following detailed description, which references and incorporates FIGS. 1–4, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1:
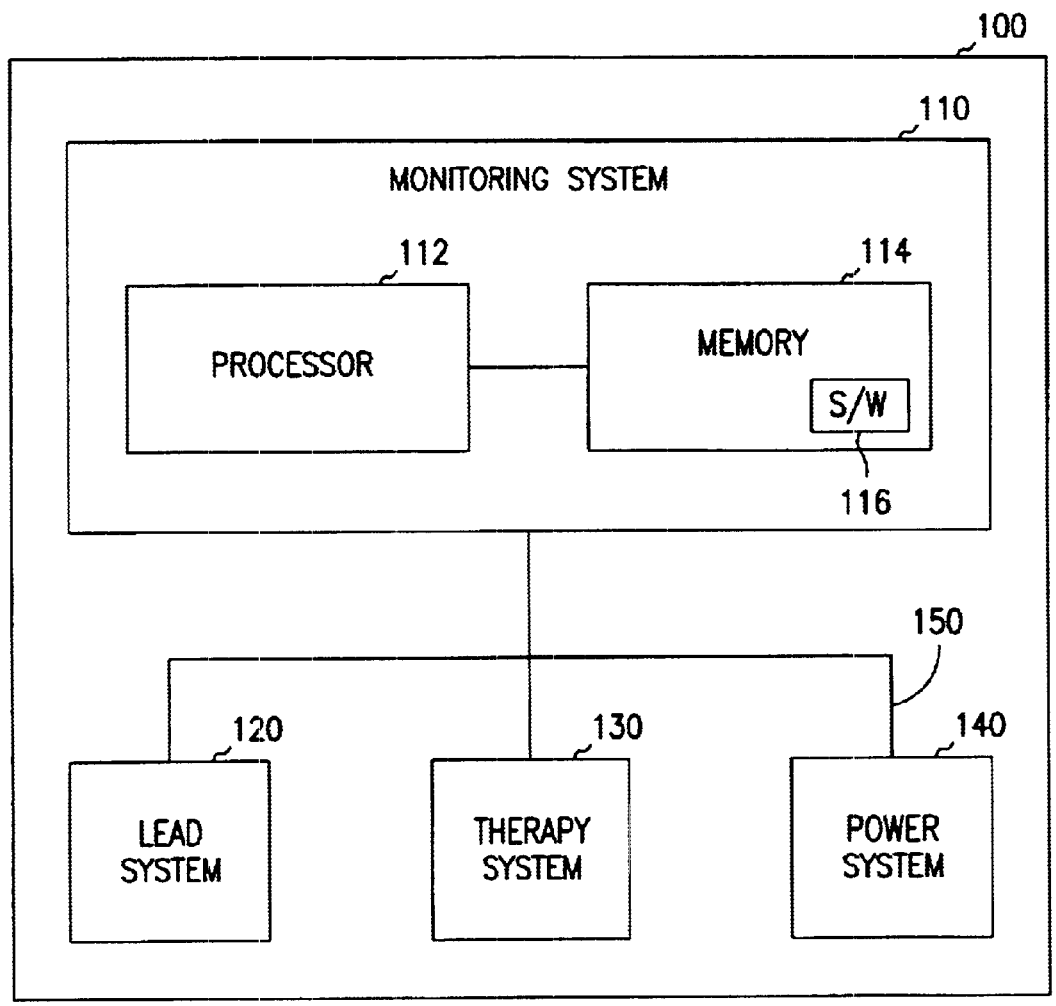
FIG. 1 is a block diagram of an exemplary implantable heart monitor incorporating teachings of the present invention.

FIG. 1 shows an exemplary implantable heart-monitoring device (or pulse generator) 100 incorporating teachings of the present invention. Device 100 includes a monitoring system 110, a lead system 120, a therapy system 130, a power system 140, and an interconnective bus 150. Monitoring system 110 includes a processor or microcontroller 112 and a memory 114. Memory 114 includes one or more software modules 116 which store one or more computer instructions in accord with the present invention. Some embodiments of the invention replace software modules 116 with one or more hardware or firmware modules. In the exemplary embodiment, processor 112 is a ZiLOG™ Z80 microprocessor (with a math coprocessor), and memory 114 is a read-only memory. However, the invention is not limited to any particular microprocessor, microcontroller, or memory.

Lead system 120, in the exemplary embodiment, includes one or more electrically conductive leads—for example, atrial, ventricular, or defibrillation leads —suitable for insertion into a heart. One or more of these are suitable for sensing electrical signals from a portion of the heart and one or more are suitable for transmitting therapeutic doses of electrical energy. Lead system 120 also includes associated sensing and signal-conditioning electronics, such as atrial or ventricular sense amplifiers and/or analog-to-digital converters, as known or will be known in the art.

In some embodiments, lead system 120 supports ventricular epicardial rate sensing, atrial endocardial bipolar pacing and sensing, ventricular endocardial bipolar pacing and sensing, epicardial patches, and Endotak® Series and ancillary leads. In some embodiments, lead system 120 also supports two or more pacing regimens, including DDD pacing. Also, some embodiments use a housing for device 100 as an optional defibrillation electrode. The invention, however, is not limited in terms of lead or electrode types, lead or electrode configurations, pacing modes, sensing electronics, or signal-conditioning electronics.

Therapy system 130 includes one or more capacitors and other circuitry (not shown) for delivering or transmitting electrical energy in measured doses through lead system 120 to a heart or other living tissue. In the exemplary embodiment, therapy system 130 includes aluminum electrolytic or polymer-based capacitors. However, other embodiments use one or more other devices for administering non-electrical therapeutic agents, such as pharmaceuticals, to a heart. Thus, the invention is not limited to any particular type of therapy system.

In general operation, lead system 120 senses atrial or ventricular electrical activity and provides data representative of this activity to monitoring system 110. Monitoring system 110, specifically processor 112, processes this data according to instructions of software module 116 of memory 114. If appropriate, processor 112 then directs or causes therapy system 130 to deliver one or more measured doses of electrical energy or other therapeutic agents through lead system 120 to a heart.

Figure 2:
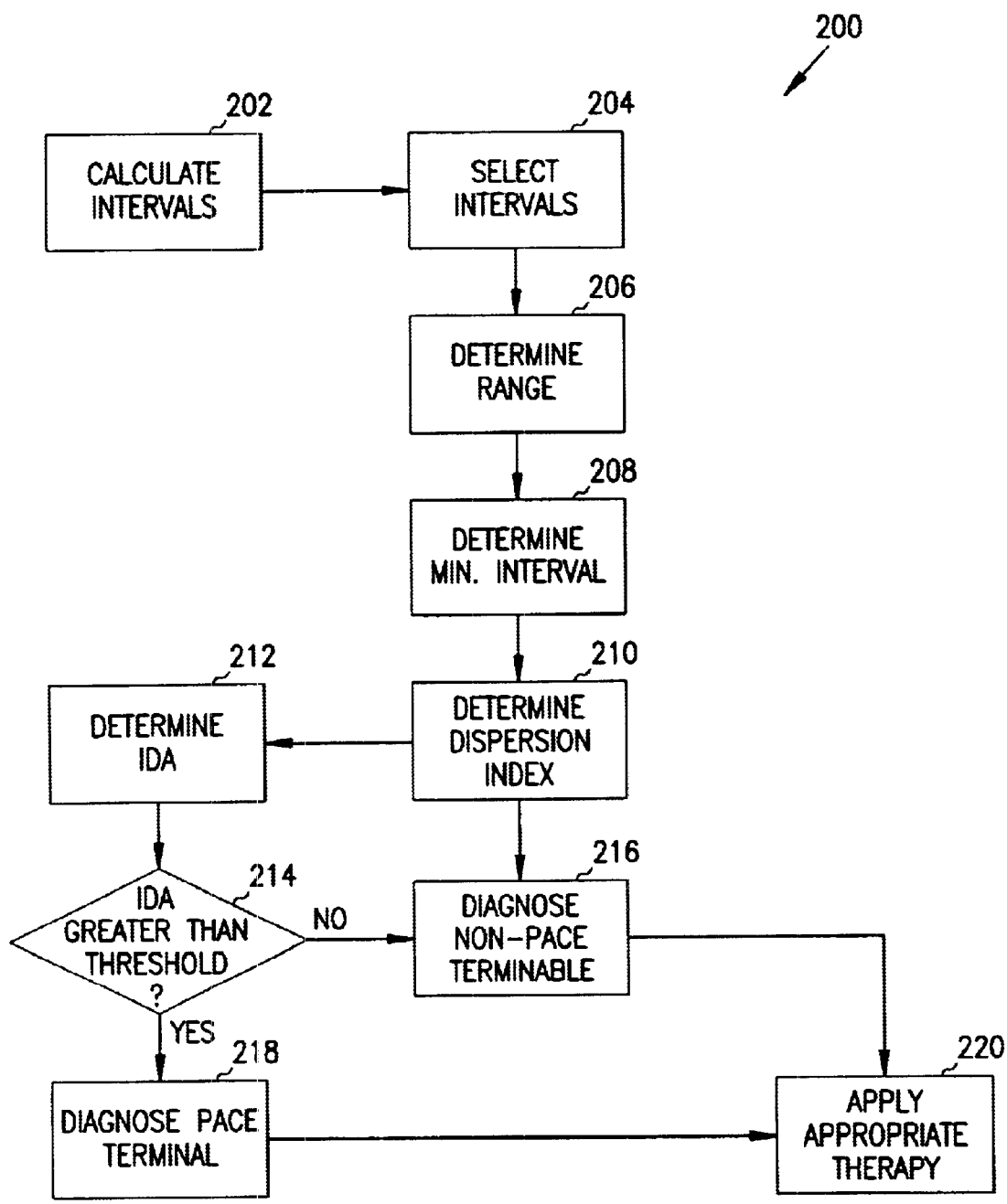
FIG. 2 is a flow chart illustrating an exemplary method incorporating teachings of the present invention.

FIG. 2, which shows an exemplary flow chart 200, illustrates an exemplary data-processing method embodied within software module 116 and executed by processor 112. Flow chart 200 includes blocks 202–220, which are arranged serially in the exemplary embodiment. However, other embodiments of the invention may execute two or more blocks in parallel using multiple processors or a single processor organized as two or more virtual machines or subprocessors. Moreover, still other embodiments implement the blocks as two or more specific interconnected hardware modules with related control and data signals communicated between and through the modules. For example, block 206 can be built as a range-determination module, block 208 as a minimum-interval-determination module 208, block 210 as a dispersion-index-determination module 210, and block 212 as an interval-assessment module 212 which receives inputs from modules 208–210 and outputs a signal or quantity based on these inputs. Thus, the exemplary process flow is instructive to software, firmware, and hardware implementations.

In process block 202, processor 112 of device 100, receives data representative of all or part of an electrogram, including atrial (or ventricular) electrical activity. From this data, the processor calculates the time between successive atrial (or ventricular) depolarizations. In other words, the processor computes a set of pp-intervals (or atrial intervals) from the electrogram, with each pp-interval based on the time between one atrial depolarization and the next occurring atrial depolarization in the electrogram. Other embodiments compute intervals based on other generally recurrent features in the electrogram.

At process block 204, the processor selects a predetermined number Y of the computed intervals for further processing, thereby defining a data window. For example, one embodiment extracts the last 12 consecutive intervals; another extracts the first or last 48 consecutive intervals; and yet another extracts the last or first 3 or 6 consecutive intervals. The selection process, in the exemplary embodiment, also entails sorting the computed intervals by magnitude and rejecting a certain number of the smallest intervals, for example the two smallest, and a certain number of the largest intervals, for example the two largest. Thus, the present invention is not limited to any particular number of intervals or to any particular scheme of selecting these intervals.

As shown in process blocks 206, 208, and 210, the processor then uses the set of Y intervals to calculate three statistics. In block 206, the processor determines the range of the last Y intervals, that is, the time, or temporal distance, between the earliest or first intervals and the most-recent or last interval included in the set of Y intervals. Some embodiments define and calculate the range based the time between the average of a first subset of the intervals and the average of a second subset of the intervals.

Thus, for example, one embodiment averages the earliest or first three intervals to determine a first composite interval, averages the latest or last three intervals to determine a second composite interval, and then computes the range as the difference of the first and second composite intervals. Moreover, variations of this embodiment, average the intervals using a weighted averaging scheme to give one or more of the intervals greater or lesser significance within the resulting composite interval.

Still other embodiments replace the range statistic with stability measurements as used in the existing Ventak™ family of devices manufactured by Guidant Corporation of St. Paul, Minn. Stability measurments are weighted averages of the differences between successive intervals. For example, if there are three intervals, one stability measurment would be the average of the difference of the first and second intervals and the difference of the second and third intervals. Weights may be chosen to emphasize or deemphasize the relative importance of certain intervals, for example, older or younger intervals.

In block 208, the processor determines a minimum interval from the set of Y intervals. In the exemplary embodiment, the processor selects the smallest interval in the set of Y intervals. However, in other embodiment, determining the minimum interval entails averaging two or more of the smallest intervals and/or selecting a minimum interval from a subset of the Y intervals. For example, some embodiments reject one or more of the intervals as a false interval, based on their length, to prevent them from corrupting the process of determining a minimum interval.

Block 210 entails determining a third statistic, that is, a dispersion index, based on the distribution or dispersion of the set of the Y intervals. The exemplary embodiment computes this dispersion index as the variance or standard deviation of all or a portion of the Y intervals. More specifically, computing the variance entails computing a mean, or average, interval using the relevant intervals, summing the squares of the interval deviations from the average interval (that is, subtracting the mean interval from each relevant interval to obtain a difference, squaring each difference, and adding the squared differences together), and dividing the total sum of these squares by the number of relevant intervals. Variance can be succinctly expressed as $$\text{Variance} = (N-1)^{-1} * \sum\nolimits^{N} (Y_i - Y_{mean})^2, \quad \text{Eq. (1)}$$

where N denotes the number of relevant intervals, $\Sigma^N$ denotes summation over the N relevant intervals, $Y_i$ denotes the i-th one of the relevant intervals, and $Y_{mean}$ denotes the means, or average, of the N relevant intervals. (In some embodiments, N, the number of relevant intervals, is not equal to Y.) Standard deviation is defined as the positive square root of Variance.

Other embodiments of the invention use other methods to quantify dispersion. For example, one embodiment weights one or more of the intervals to give these intervals more or less significance in an otherwise conventional calculation of variance or standard deviation. Another embodiment, simply averages the absolute deviation of each relevant interval from a mean interval or from a selected one of the relevant intervals, such as the median interval. Still other embodiments of the invention use other measures of interval variation about some other parameter or measure. For example, one can generalize from the use of variance, which is a second order moment about the means of a sample set, to use higher, that is, third, fourth, and so forth, moments about the mean or another desirable quantity. Other embodiments also use versions of a stability measurement.

After calculation of the dispersion index, execution of the exemplary method proceeds to process block 212. In block 212, the processor calculates a scalar quantity, which the inventor defines as an interval dispersion assessment (IDA), based on the three statistics. In the exemplary embodiment, this entails evaluating a predetermined scalar function at the three statistics. Mathematical, this is expressed as $$\text{IDA} = f(\text{Range, Min\_interval, Dispersion\_index}), \quad \text{Eq. (2)}$$

where f denotes a predetermined function including at least three variables, or degrees of freedom.

More particularly, the inventor has devised two exemplary scalar functions. In a first exemplary scalar function, the IDA is directly proportional to the range and the dispersion index and inversely proportional to the minimum interval. In mathematical terms, this is expressed as $$\text{IDA}_1 = K*\text{Range}*\text{Dispersion\_index}*(\text{Min\_interval})^{-1} \quad \text{Eq. (3)}$$

where K is a constant, Range denotes the range statistic calculated in block 208, Dispersion_index represents the dispersion index calculated in block 210, and Min_interval is the statistic calculated in block 206. An exemplary value for K is unity.

In a second exemplary scalar function, the processor computes the AIDA according to the following equation:

$$\text{IDA}_2 = K_1*\text{Range} + K_2*\text{Dispersion\_index} + K_3* \\ (\text{Min\_interval})^{-1} \quad \text{Eq. (4)}$$

where $K_1$, $K_2$, and $K_3$ are constants. Thus, the second exemplary scalar function defines the IDA as a weighted sum of the range, dispersion index, and minimum interval. Exemplary values for $K_1$, $K_2$, and $K_3$ are respectively 0.0001, 0.0001, and 1.00. The Min_interval term in equation (4) is indicative of a maximum rate of depolarization. If $K_3$ equals 6000, then this term will equal the maximum rate.

The three statistics, range, minimum interval, and dispersion index can be combined in an unlimited number of ways to derive an IDA. For example, one embodiment averages $\text{IDA}_1$ and $\text{IDA}_2$ to determine another IDA, and another simply adds them or portions of them together to determine another IDA. Thus, the invention is not limited to any particular form of mathematical combination.

After calculating one or more IDAs, the exemplary method proceeds to process block 214, which entails comparing at least one calculated IDA to a therapy threshold. If the IDA is greater than the therapy threshold, it indicates a first heart condition, such as atrial or ventricular flutter, and the processor branches to block 218 at which it directs therapy system 130 to diagnose the current rhythmic state as pace-terminable, which means that pacing pulses are likely to restore normal heart function. If the IDA is less than the therapy threshold, it indicates a second heart condition, such as atrial or ventricular fibrillation, and the processor branches to block 216 to diagnose the current rhythmic state as non-pace terminable, meaning that pacing pulses are not likely to restore normal heart function. An exemplary therapy threshold for discerning atrial flutter and atrial fibrillation using the first exemplary IDA is 2.25 or 5.0, and an exemplary threshold for discerning atrial flutter and atrial fibrillation using the second IDA is 0.001 or 2.25. Generally, one can determine therapy thresholds for an IDA in accord with the present invention, through experimentation using actual heart data.

After making the appropriate diagnosis in block 216 or block 218, the processor executes block 220, directing therapy system 130 to apply a therapy appropriate for the classification of the current rhythmic state represented by the intervals. The inventor forecasts that the use of the interval dispersion assessment as a determinant of therapy choice will ultimately result in more accurate therapy choices than is possible with algorithms of similar complexity. Moreover, the accuracy of the exemplary interval dispersion assessment or other versions may even rival that of more complex algorithms while saving considerable power and processing time.

The comparison of the scalar IDA to scalar threshold is a very simple way of discerning one condition from another condition, for example, atrial flutter or ventricular tachycardia from atrial or ventricular fibrillation. However, another aspect of the invention stems from realization that equations (3) and (4), which are used to compute the exemplary IDAs, can be set equal to a threshold value to define a set of ordered triples, which actually define surfaces in a three-dimensional space. For example, FIGS. 3 and 4 show three-dimensional surfaces developed by setting each of the functions equal to an exemplary threshold values and evaluating them over specific domains of interval range, minimum intervals, and dispersion indices.

Figure 3:
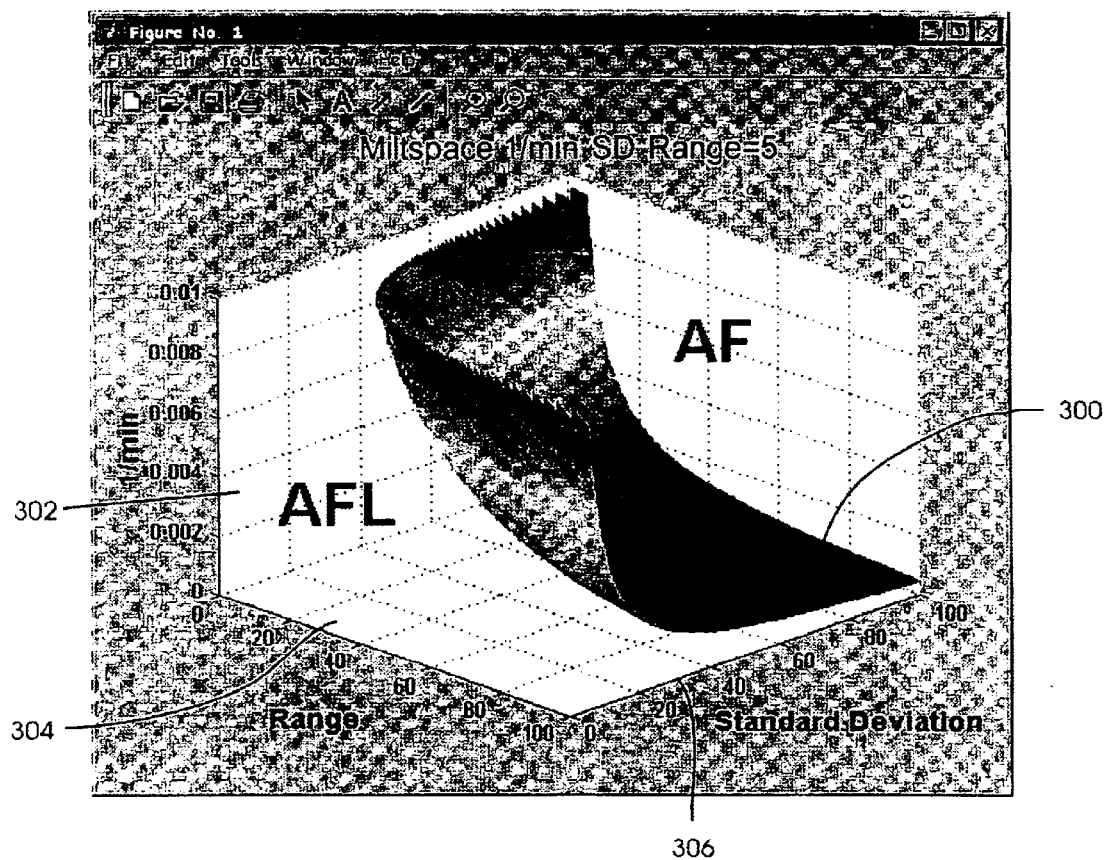
FIG. 3 is an exemplary graph of a three-dimensional function incorporating teachings of the present invention.
Figure 4:
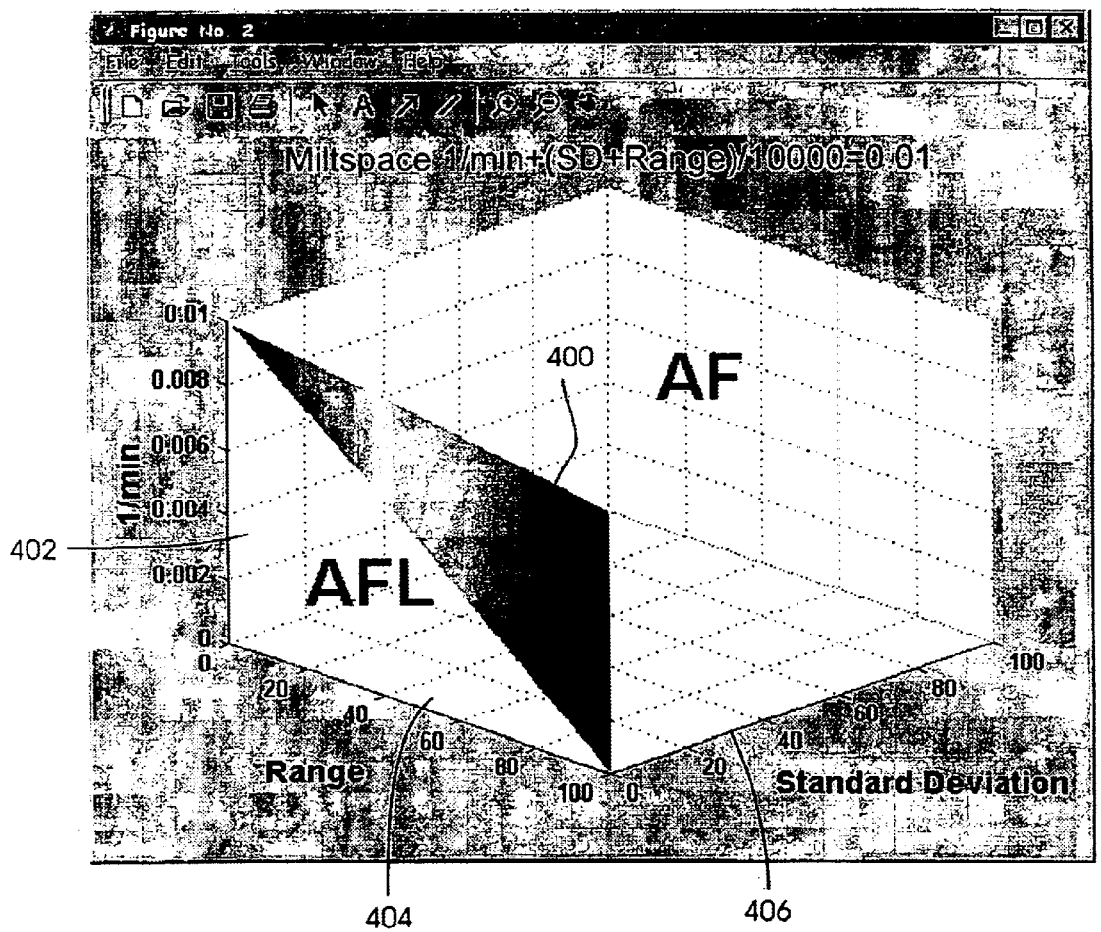
FIG. 4 is exemplary graph of another three-dimensional function incorporating teachings of the present invention.

More specifically, FIG. 3 shows a surface 300 plotted in the three-dimensional spaced by an inverse-minimuminterval axis 302, a range axis 304, and a dispersion axis 306. Surface 300 represents a set of minimum intervals, ranges, and dispersions indices which jointly make equation (3) equal 5, with K equal 1. Similarly, FIG. 4 shows a surface 400 plotted in a space defined by an inverse-minimum-interval axis 402, a range axis 404, and a dispersion axis 406. Surface 300 represents a set of minimum intervals, ranges, and dispersions indices which jointly make equation (4) equal 0.01, with $K_1$, $K_2$, and $K_3$ respectively 0.0001, 0.0001, and 1.00.

Surface 300 and surface 400 divide their respective spaces into two subspaces. One subspace, denoted AF1 for atrial flutter, contains points generated from pace terminable rhythms, and the other subspace, denoted AF for atrial fibrillation, contains points that are non-pace terminable. Thus, in some embodiments, which provide a graphical display for displaying surface 300 or 400, the relation of a point to the surface can be used to diagnose rhythmic states. If an IDA point lies above surface 300 or 400, the processor deems the rhythm that produced the IDA, for example, certain atrial fibrillations, as non-pace terminable. Conversely, if the IDA point lies below the surface or oscillates above and below the surface over time, the processor deems the associated rhythm pace terminable.

Thus, the three statistics that the exemplary embodiment uses to define an IDA also define a point in a three-space which lies on the surface or on either side of the surface. One can therefore discriminate a condition using its coordinate position relative to a linear or non-linear surface. Similarly, one can choose two of the three statistics and define a line of demarcation in a two-space defined by ordered pairs of the chosen two statistics.

In some embodiments, implantable device 100 includes a wireless transceiver, which permits use of an external programmer to interrogate and program device 100 via bi-directional radio communications. At a minimum, this allows adjustment of one or more of the thresholds and other parameters defining an IDA. These thresholds and parameters can then be set and changed based on observations of a specific patient or group of patients. In other embodiments, the inventor contemplates replacing or supplementing an existing software module or algorithm with one in accord with the present invention. In still other embodiments, the exemplary methods are used to classify atrial rhythms which are, for example, between 100 and 200 beats per minute, inclusive.

Conclusion

In furtherance of the art, the inventor devised new methods for processing data representative of a heart electrogram and selecting appropriate therapy options. An exemplary embodiment of the method entails computing three statistics—a range statistic, a minimum interval statistic, and a dispersion index—from a set of depolarization (or polarization) intervals. More particularly, the exemplary embodiment defines the range statistic as the difference between a first and second one of the depolarization intervals, the minimum interval as the smallest of a subset the intervals, and the dispersion index as the standard deviation of the intervals. The exemplary embodiment then uses the three statistics to compute a scalar interval dispersion assessment (IDA), which it compares to a threshold to identify an appropriate therapy option. Ultimately, the exemplary method and other methods incorporating teachings of the present invention, can be incorporated into an implantable medical device, for example, a defibrillator or a cardioverter defibrillator, to identify and treat abnormal rhythmic conditions efficiently and accurately. The teachings of the present invention can also be incorporated into other applications which require classification of system conditions or states based on recurrent events.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. Apparatus for monitoring heart activity in an implantable medical device, the apparatus comprising:
   means for calculating a set of two or more intervals based on measured heart activity;
   means for determining a minimum interval based on the set of two or more intervals;
   means for calculating a range statistic based on a difference between a first subset and second subset of the intervals;
   means for calculating a dispersion index based on a subset of the intervals;
   means for calculating a member based on the minimum interval, the range statistic, and the dispersion index; and
   means for comparing the number to a threshold to determine a therapy option.

2. The monitoring apparatus of claim 1, wherein the first subset of the intervals includes only a first one of the intervals and the second subset of the intervals includes only a second one of the intervals.

3. The monitoring apparatus of claim 1, wherein each of the set of two or more intervals is an atrial depolarization interval.

4. The monitoring apparatus of claim 1, wherein the means for calculating a number based on the minimum interval, the range statistic, and the dispersion index computes the number based on an function having one of the following forms:

$$IDA_1 = K*Range*Dispersion\_index*(Min\_interval)^{-1}$$

$$IDA_2 = K_1*Range + K_2*Dispersion\_index + K_3*(Min\_interval)^{-1},$$

where K, $K_1$, $K_2$, and $K_3$ denote constants; Range denotes the range statistic;
Dispersion_index denotes the dispersion index; and Min_interval denotes the minimum interval.

5. The monitoring apparatus of claim 4, wherein K and $K_3$ are each approximately 1.0, and wherein $K_1$ and $K_2$ are each approximately 0.0001.

6. Apparatus for monitoring heart activity, comprising:
   a minimum-interval-determination module to determine a minimum interval from a set of two or more intervals based on sensed heart activity;
   a range-determination module to determine a range parameter based on a difference between a first subset and second subset of the intervals;
   a dispersion-determination module to determine a dispersion parameter quantifying dispersion of a subset of the intervals;
   an assessment-determination module coupled to the minimum-interval-determination module, the range-determination module, and the dispersion-indexdetermination module to determine an assessment value for the set of intervals, based on the minimum interval, the range parameter, the dispersion index; and a decision module coupled to the assessment-calculation to make a decision based on the determined assessment value.

7. The apparatus of claim 6, wherein the decision is based on a comparison of the determined assessment value and a threshold.

8. A method of selecting one of at least first and second cardiac therapy options, the method comprising:

calculating a set of two or more intervals based on data indicative of heart activity;

selecting a subset of intervals from the set of intervals, with the subset including at least two intervals;

determining a minimum interval based on the subset of intervals;

determining a range parameter based on a difference between a first interval in the subset and a second interval in the subset;

determining a dispersion parameter based on the subset of intervals;

determining an assessment parameter based on the minimum interval, the range parameter, and the dispersion parameter; and selecting the first or second therapy option based on the assessment parameter.

9. The method of claim 8, wherein the range parameter is based on the minimum interval and the maximum interval in the subset.

10. The method of claim 8, wherein each of the set of two or more intervals is an atrial depolarization interval.

11. The method of claim 8, wherein the assessment parameter is inversely proportional to the duration of the minimum interval and directly proportional to the range parameter and to the dispersion parameter.

12. The method of claim 8, wherein determining the assessment parameter includes calculating $$K*Range*Dispersion*(Min\_interval)^{-1}$$

where K denote a constants; Range denotes the range parameter, Dispersion denotes the dispersion; and Min_interval denotes the minimum interval.

13. The method of claim 8, wherein the assessment parameter is based on a sum of at least first, second, and third components, with the first component directly proportional to the range parameter, the second component directly proportional to the dispersion parameter, and the third component inversely proportional to the duration of the minimum interval.

14. The method of claim 8, wherein calculating the assessment parameter includes calculating $$K_1*Range+K_2*Dispersion+_3*(Min\_interval)^{-1},$$

where $K_1$, $K_2$, and $K_3$ denote constants; Range denotes the range parameter; Dispersion denotes the dispersion parameter; and Min_interval denotes the minimum interval.

15. The method of claim 14, wherein $K_3$ is approximately 1.0, and wherein $K_1$ and $K_2$ are each approximately 0.0001.

16. A method of selecting a therapy option in a medical device, comprising:

defining a surface in a space having at least three dimensions;

calculating a set of two or more intervals based on data representative of at least a portion of an electrogram;

calculating a minimum interval based on the set of intervals;

calculating a range parameter based on a first subset and a second subset of the intervals;

calculating a dispersion parameter based on a subset of the intervals;

defining a point in the space based on the minimum interval, the range parameter, and the dispersion parameter; and selecting one of at least two therapy options based on position of the point relative to the surface.

17. A method of selecting a therapy option in a medical device, comprising:

defining a surface in a space having at least three dimensions;

calculating a set of two or more intervals based on data representative of at least a portion of an electrogram calculating a minimum interval based on the set of intervals;

calculating a range parameter based on a first subset and a second subset of the intervals;

calculating a dispersion parameter based on a subset of the intervals;

defining a point in the space based on the minimum interval, the range parameter, and the dispersion parameter; and selecting one of at least two therapy options based on positions of the point relative to the surface, wherein the assessment parameter is inversely proportional to the duration of the minimum interval and directly proportional to the range parameter and to the dispersion parameter.

18. A method of selecting a therapy option in a medical device, comprising:

defining a surface in a space having at least three dimensions;

calculating a set of two or more intervals based on data representative of at least a portion of an electrogram;

calculating a minimum interval based on the set of intervals;

calculating a range parameter based on a first subset and a second subset of the intervals;

calculating a dispersion parameter based on a subset of the intervals;

defining a point in the space based on the minimum interval, the range parameter, and the dispersion parameter; and selecting one of at least two therapy options based on position of the point relative to the surface, wherein the assessment parameter is based on a sum of at least first, second, and third components, with the first component directly proportional to the range parameter, the second component directly proportional to the dispersion parameter, and the third component inversely proportional to the duration of the minimum interval.

19. A method of selecting a therapy option in a medical device, comprising:

defining a surface in a space having at least three dimensions;

calculating a set of two or more intervals based on data representative of at least a portion of an electrogram;

calculating a minimum interval based on the set of intervals;

calculating a range parameter based on a first subset and a second subset of the intervals;

calculating a dispersion parameter based on a subset of the intervals;

defining a point in the space based on the minimum interval, the range parameter, and the dispersion parameter; and selecting one of at least two therapy options based on position of the point relative to the surface;

wherein the assessment parameter is based on a sum of at least first, second, and third components, with the first component directly proportional to the range parameter, the second component directly proportional to the dispersion parameter, and the third component inversely proportional to the duration of the minimum interval; and wherein calculating the assessment parameter includes calculating $$K * Range * Dispersion * (Min\_interval)^{-1}$$

where K denote a constant; Range denotes the range parameter; Dispersion denotes the dispersion parameter; and Min_interval denotes the minimum interval.

* * * * *

UNITED STATES PATENT AND TRADEMARK OFFICE
CERTIFICATE OF CORRECTION

PATENT NO. : 6,681,134 B2
DATED : January 20, 2004
INVENTOR(S) : Morris

It is certified that error appears in the above-identified patent and that said Letters Patent is hereby corrected as shown below:

Title page,
Item [56], References Cited, FOREIGN PATENT DOCUMENTS, after "4/1995" insert -- A61N --.
OTHER PUBLICATIONS, reference "Jung, et al.," after "Jung," insert -- J., --.

Column 8,
Line 25, delete "member" and insert -- number -- therefor.
Line 40, delete "an" and insert -- a --, therefor.

Column 9,
Line 43, delete "denote a constants" and insert -- denotes a constant --, therefor.
Line 44, delete "," and insert -- ; --, therefor.
Line 56, delete "$K_1*Range+K_2*Dispersion+_3*(Min\_interval)^{-1}$," and insert
-- $K_1*Range+K_2*Dispersion+ K_3*(Min\_interval)^{-1}$, -- therefor.

Column 10,
Line 20, after "electrogram" insert -- ; --.
Line 32, delete "positions" and insert -- position --, therefor.

Column 12,
Line 11, delete "denote" and insert -- denotes --, therefor.

Signed and Sealed this

Sixth Day of July, 2004

JON W. DUDAS
*Acting Director of the United States Patent and Trademark Office*